United States Patent [19]

Tieman

[11] 4,302,592

[45] Nov. 24, 1981

[54] PESTICIDAL 3-(2,3-DIHYDROBENZOFURAN-7-yl)-5-METHOXY-1,3,4-OXADIAZOL-2(3H)-ONE

[75] Inventor: Charles H. Tieman, Modesto, Calif.

[73] Assignee: Shell Oil Company, Houston, Tex.

[21] Appl. No.: 187,240

[22] Filed: Sep. 15, 1980

[51] Int. Cl.³ .................... A01N 43/82; C07D 271/10
[52] U.S. Cl. .............................. 548/144; 260/346.22; 260/346.72; 424/272
[58] Field of Search ........................ 548/144; 424/272

[56] References Cited

U.S. PATENT DOCUMENTS

| | | | |
|---|---|---|---|
| 3,772,323 | 11/1973 | Schlapfer et al. | 548/143 |
| 3,971,803 | 7/1976 | Rosenberger et al. | 548/144 |
| 4,076,824 | 2/1978 | Boesch | 548/144 |
| 4,150,142 | 4/1979 | Boesch | 548/144 |

Primary Examiner—Alton D. Rollins

[57] ABSTRACT

3-(2,3-dihydrobenzofuran-7-yl)-5-methoxy-1,3,4-oxadiazol-2-(3H)-one, useful as a pesticide.

1 Claim, No Drawings

PESTICIDAL 3-(2,3-DIHYDROBENZOFURAN-7-yl)-5-METHOXY-1,3,4-OXADIAZOL-2(3H)-ONE

DESCRIPTION OF THE INVENTION

It has been found that useful pesticidal properties are possessed by 3-(2,3-dihydrobenzofuran-7-yl)-5-methoxy-1,3,4-oxadiazol-2(3H)-one, of the formula

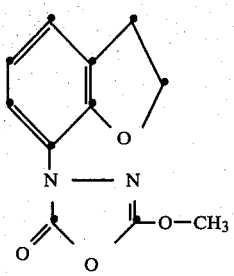

For the sake of brevity, this compound will henceforth herein be designated as Compound A.

Compound A has been prepared as shown in Example 1. The identity of each intermediate but one, and of Compound A, was confirmed by appropriate chemical and spectral analyses.

EXAMPLE 1 a. Preparation of 2,3-dihydro-7-benzofuranamine (1)

39.4 g of 2,3-dihydro-7-nitrobenzofuran (prepared by the method described in Journal of Heterocyclic Chemistry, vol. 5, No. 1, p. 1 (1968)) in 200 ml of tetrahydrofuran was hydrogenated in a Parr shaker (50 p.s.i.g. hydrogen pressure, Raney nickel catalyst, 3 hours, room temperature). The resulting mixture was filtered and the solvent was evaporated from the filtrate. The residue was recrystallized from ether to give 1, as a colorless solid, m.p.: 70°–72° C.

b. (2,3-dihydrobenzofuran-7-yl)diazenesulfonic acid, sodium salt, monohydrate (2)

25 g of 1 was added to a solution of 65 ml of concentrated hydrochloric acid in 200 ml of water. The mixture was warmed to 45° C., and then stirred at room temperature for 18 hours. The mixture was chilled to 5° C. during the addition (over a period of 20 minutes) of a solution of 14 g of sodium nitrite in 20 ml of water. The resulting mixture was stirred at 45° C. for 45 minutes, then added drop-by-drop over a period of 15 minutes to a mixture of 164 g of sodium sulfite and 315 ml of water, at 5°–10° C. The mixture was stirred at room temperature for 3 hours. A sample of the product (2), a yellow solid, m.p.: approximately 180° C. (with decomposition), was isolated for analysis and the remaining mixture was used in step (c).

c. 2-(2,3-dihydrobenzofuran-7-yl)hydrazinesulfonic acid, potassium salt (3)

A solution of 32.2 g of sodium dithionite in 100 ml of water was added drop-by-drop over a period of 15 minutes, with stirring, at 25° C., to the final mixture of step (b). The resulting mixture was stirred for 2 hours at room temperature, then at 70° C. for 10 minutes. Then, 148 g of potassium chloride was added and the mixture was stirred for 18 hours. The resulting mixture was chilled to 5° C. and filtered. The solid was dried to give 3, m.p.: 255° C. (with decomposition).

d. 7-hydrazino-2,3-dihydrobenzofuran hydrochloride (4)

A mixture of 45.3 g of 4 and 500 ml of anhydrous methanol was chilled to 5°–10° C. during the addition of 23 g of anhydrous hydrochloric acid, stirred at room temperature for 18 hours, and filtered. The solvent was evaporated from the filtrate, the residue being 4.

e. 3-(2,3-dihydrobenzofuran-7-yl)hydrazinecarboxylic acid, methyl ester (5)

A mixture of 30 g of 4, 150 ml of tetrahydrofuran and 24.5 g of ethyldiisopropylamine was chilled to 5° C. while 5.1 g of methyl chloroformate was added drop-by-drop over a period of 10 minutes. The resulting mixture was stirred for 30 minutes at 5° C., then warmed to and held at 60° C. for 10 minutes. The volatile materials were evaporated. The residue was taken up in 300 ml of water and extracted with ether. The extract was dried ($MgSO_4$) and the solvent was partially evaporated. The residue was chilled and filtered to give 5, as an off-white solid, m.p.: 110°–112° C.

f. 2-(chlorocarbonyl)-2-(2,3-dihydrobenzofuran-7-yl)hydrazinecarboxylic acid, methyl ester (6)

A solution of 3.5 g of 5 in 25 ml of benzene was added drop-by-drop over a period of 5 minutes at room temperature to a stirred solution of 5 g of phosgene in 75 ml of benzene. The mixture was refluxed for one hour, the solvent was evaporated, and the residue was crystallized from methanol to give 6, as a colorless solid, m.p.: 110°–112° C.

g. Compound A 0.123 g of 6 was mixed with 2 ml of methanol and 0.1 ml of triethylamine and the mixture was allowed to stand overnight. The mixture was diluted with ether, washed with dilute hydrochloric acid, and dried ($MgSO_4$), and the solvent was evaporated. The residue was purified by thin layer chromatography to give Compound A, as a creamcolored solid; m.p.: 108°–109° C.

Activity of Compound A with respect to insect pests was determined by using standardized test methods to test the toxicity of the compound as follows:

I. Houseflies (*Musca domestica* (Linne)) were tested by placing 50 4- to 5-day old houseflies into a spray cage and spraying with 0.6 ml of a solution of test compound. After spraying, the flies were anesthetized with $CO_2$ and transferred to a recovery cage containing a milk pad for food. The cages were held for 18–20 hours after which mortality counts were made. Both dead and moribund flies were counted. The tests were conducted employing several different dosage rates for Compound A.

II. Pea aphids (*Acyrthosiphon pisum* (Harris)) were tested by placing about 100 aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for Compound A.

III. Corn earworm larvae (*Heliothis zea* (Boddie)) were tested by spraying a broad bean plant with dilutions of an acetone solution of the test compound in water containing an emulsifier. Immediately after spraying, 5 larvae were transferred to the plant and held for 44-46 hours, at which time the dead and moribund larvae were counted. The tests were conducted employing several different dosage rates for the test Compound A.

In the case of each species of insect, the concentration of the test Compound A in the formulation required to kill fifty percent of the test insects—i.e., the $LC_{50}$ dosage—was determined. The results are set out in Table I.

TABLE I

|  | $LC_{50}$ | | |
|---|---|---|---|
|  | House-fly | Pea Aphid | Corn Earworm |
| Compound A | 0.05 | 0.0006 | 0.023 |

Compound A of the invention can be used to control pests at a locus to be protected by applying to that locus a suitable pesticidal composition containing it. The composition comprises an adjuvant—that is, a carrier, and optionally a surface-active agent—and, as active ingredient, Compound A. Likewise, the invention includes also a method of combatting insect pests at a locus which comprises applying to the locus an effective amount of Compound A.

The term "carrier" as used herein means a solid or fluid material, which may be inorganic or organic and of synthetic or natural origin, with which the active compound is mixed or formulated to facilitate its application to the plant to be treated, or its storage, transport or handling.

Suitable solid carriers are natural and synthetic clays and silicates, for example, natural silicas such as diatomaceous earths; magnesium silicates, for example talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing $\frac{1}{2}$-10% by weight of toxicant. Granules are usually prepared to have a size between 10 and 100 BS mesh (1.676-0.152 mm), and may be manufactured by agglomeration or impregnation techniques. Generally, granules will contain $\frac{1}{2}$-25% by weight toxicant and 0-1% by weight of additives such as stabilizers, slow release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight toxicant, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate, also are comtemplated. The said emulsions may be of the water-in-oil or the oil-in-water type, and may have a thick mayonnaise-like consistency.

The compositions may also contain other ingredients, for example, other compounds possessing pesticidal, especially insecticidal, acaricidal, herbicidal or fungicidal properties.

The method of applying Compound A to control pest comprises applying it, ordinarily in a composition of one of the aforementioned types, to a locus to be protected from the pests, such as the foliage and/or the fruit of plants. It is of course applied in an amount sufficient to exert the desired action. This dosage is dependent upon many factors, including the carrier employed, the method and conditions of the application, whether the formulation is present at the locus in the form of an aerosol, or as a film, or as discrete particles, the thickness of film or size of particles, and the like, proper consideration and resolution of these factors to provide the necessary dosage of active material at the locus to be protected being within the skill of those versed in the art. In general, however, the effective dosage of Compound A at the locus to be protected—i.e., the dosage which the pests contact—is of the order of 0.001 to 0.05% based on the total weight of the formulation, though under some circumstances the effective concentration will be as little as 0.0001% or as much as 2%, on the same basis.

I claim:

1. 3-(2,3-dihydrobenzofuran-7-yl)-5-methoxy-1,3,4-oxadiazol-2(3H)-one.

* * * * *